United States Patent
Fan et al.

(10) Patent No.: US 12,030,830 B1
(45) Date of Patent: Jul. 9, 2024

(54) METHOD OF PREPARING OLEFINS FROM METHANOL

(71) Applicant: ZHEJIANG UNIVERSITY, Hangzhou (CN)

(72) Inventors: Jie Fan, Hangzhou (CN); Baohui Lou, Hangzhou (CN); Yue Wang, Hangzhou (CN); Shihui Zou, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 18/545,426

(22) Filed: Dec. 19, 2023

Related U.S. Application Data (63) Continuation of application No. PCT/CN2023/094587, filed on May 16, 2023.

(30) Foreign Application Priority Data

Apr. 14, 2023 (CN) .......................... 202310399567.X (51) Int. Cl.
| | |
|---|---|
| *C07C 1/20* | (2006.01) |
| *B01J 21/04* | (2006.01) |
| *B01J 21/10* | (2006.01) |
| *B01J 29/08* | (2006.01) |
| *B01J 29/40* | (2006.01) |
| *B01J 29/70* | (2006.01) |
| *B01J 29/85* | (2006.01) |
| *C07C 1/22* | (2006.01) |

(52) U.S. Cl.
CPC ............. *C07C 1/22* (2013.01); *B01J 21/04* (2013.01); *B01J 21/10* (2013.01); *B01J 29/082* (2013.01); *B01J 29/084* (2013.01); *B01J 29/40* (2013.01); *B01J 29/7007* (2013.01); *B01J 29/85* (2013.01); *C07C 2529/08* (2013.01)

(58) Field of Classification Search
CPC .. C07C 1/22; C07C 1/20; C07C 1/207; C07C 2529/08; C07C 2529/40; C07C 2529/70; C07C 2529/83; C07C 2529/85; B01J 21/04; B01J 21/10; B01J 29/082; B01J 29/084; B01J 29/40; B01J 29/84; B01J 29/85; B01J 29/7007
USPC ................ 585/520, 527, 638, 639, 640, 641
See application file for complete search history.

(56) References Cited

U.S. PATENT DOCUMENTS

2007/0038011 A1   2/2007   Xie et al.

FOREIGN PATENT DOCUMENTS

| CN | 1356299 A   | 7/2002 |
|---|---|---|
| CN | 101165026 A | 4/2008 |
| CN | 101402539 A | 4/2009 |
| CN | 105439788 A | 3/2016 |

(Continued)

OTHER PUBLICATIONS

Luo et al.- CN105439788, machine translation (Year: 2016).*
Internation Search Report of PCT/CN2023/094587, Mailed Aug. 28, 2023.

*Primary Examiner* — Smita S Patel (57) ABSTRACT

The present disclosure provides a method of preparing olefins from methanol, in which methanol and phenol-like molecules are used as raw material, which is gasified and then passed into a two-stage fixed-bed catalytic reactor. The raw material reacts with a catalyst A (silica-aluminum molecular sieve) and a catalyst B (silica-aluminum or phosphorus-aluminum molecular sieve) in sequence to produce ethylene.

11 Claims, 3 Drawing Sheets

(56) References Cited

FOREIGN PATENT DOCUMENTS

| | | | |
|---|---|---|---|
| CN | 113509957 | A | 10/2021 |
| CN | 115745751 | A | 3/2023 |

\* cited by examiner

METHOD OF PREPARING OLEFINS FROM METHANOL

CROSS REFERENCE

The present disclosure is a continuation-application of International (PCT) Patent Application No. PCT/CN2023/094587, filed on May 16, 2023, which claims priority of Chinese Patent Applications No. 202310399567.X, filed on Apr. 14, 2023, the entire contents of which are hereby incorporated by reference in their entirety.

TECHNICAL FIELD

The present disclosure relates to technical field of olefin preparation, and in particular to a method of preparing olefins from methanol.

BACKGROUND

Ethylene is one of the world's largest chemical products and is known as "mother of petrochemicals". The development of clean and efficient coal-to-ethene technology can help solve problems, of the existing industrial ethylene production process, such as strong oil dependence, low ethylene self-sufficiency, etc.

The core of the coal-to-ethylene technology lies in the methanol-to-olefin reaction; however, the current methanol-to-olefin process is still characterized by technical bottlenecks such as difficult product separation and short catalyst life. For example, Chinese patent CN1356299A discloses a preparation process of light olefin from methanol or dimethyl ether, where the catalyst is silica-aluminum phosphate type molecular sieve SAPO-34. In the process, a gas-solid parallel flow downstream fluidized bed ultra-short time contact reactor is adopted, in which the catalyst and raw materials are contacted and reacted, and then quickly separated in a gas-solid fast separator in a lower part of the reactor. The separated catalyst enters into a regenerator to remove the coke by air combustion and carry on another cycle reaction. The conversion of dimethyl ether or methanol by this reaction process is greater than 98%. However, the method has technical drawbacks such as low selectivity of ethylene and propylene, easy coke deposition of catalyst, and the need for repeated regeneration.

Another example is Chinese patent CN101165026A, which discloses a method of preparing ethylene and propylene from methanol or dimethyl ether, using a two-stage reactor and adding a gas separation unit, with ethylene selectivity of 47.1% and propylene yield of 36.9%. However, the subsequent separation of ethylene/propylene is a difficult problem with high energy consumption and high separation cost.

Therefore, there is an urgent need for a new methanol-to-olefin process route to achieve a high selectivity of olefins in methanol conversion and to solve problems with the existing industrial methanol-to-olefin production process, such as difficult product separation, easy coke deposition, etc.

SUMMARY OF THE DISCLOSURE

A first object of the present disclosure is to provide, in view of the deficiencies of the related technique, a method for the production of olefins from methanol, which realizes the highly selective production of olefins from methanol by introducing a phenol-like substance as a molecular catalyst.

A method of preparing olefins from methanol, comprising:

taking methanol and phenol-like molecules as raw material; gasifying the raw material and passing it into a two-stage fixed-bed catalytic reactor under an anaerobic environment, such that the reaction material is contacted with a catalyst A and a catalyst B in turn, and ethylene is generated after a reaction for a certain period of time; wherein the two-stage fixed-bed catalytic reactor comprises a first constant-temperature zone and a second constant-temperature zone; the catalyst A is placed in the first constant-temperature zone, and the catalyst B is placed in the second constant-temperature zone;

a structural formula of the phenol-like molecules is:

wherein $R^1$-$R^5$ are independently selected from one of H atom, alkyl, alkoxy, phenol hydroxyl, alcohol hydroxyl, halogen, respectively; and R' is selected from one of H atom, hydroxyl, alkoxy, alkyl, and amino;

the catalyst A is a silica-aluminum molecular sieve; the catalyst B is a silica-aluminum molecular sieve or a phosphorus-aluminum molecular sieve.

In some embodiments, a molar ratio of the methanol to phenol-like molecules is (1-8): 1, preferably (2-6):1, and most preferably 3:1.

In some embodiments, the first constant-temperature zone is at a temperature of 300-400° C., preferably 320-360° C.

In some embodiments, the second constant-temperature zone is at a temperature of 160-400° C., preferably 200-300° C.

In some embodiments, the catalyst A is one or more of X-type, Y-type, and β-type molecular sieves, preferably a NaX molecular sieve.

In some embodiments, the catalyst B is one or more of AlPO, SAPO, ZSM, Y-type molecular sieves, preferably a SAPO-type molecular sieve, most preferably a SAPO-34 or SAPO-18 molecular sieve.

In some embodiments, an inert gas can be used to assist the feed in the reaction process, specifically, the raw material is gasified and mixed with inert gas and passed into the two-stage fixed-bed catalytic reactor; the inert gas is selected from any one or more of $N_2$, He or Ar; the flow rate of the inert gas is 0-100 mL/min, preferably 20-80 mL/min, and more preferably 30-40 mL/min.

In some embodiments, a reaction pressure of the two-stage fixed-bed catalytic reactor is atmospheric pressure.

In some embodiments, a space velocity of the methanol is 3-200 kg $CH_3OH$/(kg cat. A)/h, preferably 6-80 kg $CH_3OH$/(kg cat. A)/h; the space velocity expresses a mass or volume of a reactant passing through the catalytic bed per unit of time, and is usually expressed as the mass or volume of reactants per unit of time divided by the mass or volume of the catalytic bed.

The beneficial effect of the present disclosure compared to the related technique includes the following.

The present disclosure provides a method of preparing olefins from methanol, using phenol-like molecules as a molecular catalyst, and a catalytic reaction by co-feeding methanol and the phenol-like molecules. After gasification of the raw material, the raw material can be brought into the reactor by an inert gas, and after a two-stage catalyst system, the selectivity of ethylene reaches more than 90%, which effectively solves the problem of the products separation in the current process. The economy of carbon atoms in the reaction process is up to 100%. In addition, the process described in the present disclosure has a good stability and can be operated continuously for more than 100 h. A little coke is formed in catalyst during the reaction, which solves the problem that the catalyst is required to be regenerated repeatedly. In addition, the traditional methanol-to-olefin process has a large investment and is suitable for large-scale production of olefins, whereas the process route of the present disclosure has the potential for miniaturized production and can be applied in the industrial production of ethylene with annual small-scale output.

DETAILED DESCRIPTION

The present disclosure is further illustrated below by means of embodiments, but the embodiments do not limit the present disclosure thereby.

Thorough the embodiments, reagents used are analytically pure unless otherwise specified.

Ethylene selectivity and ethylene yield for 100 hours of continuous operation (abbreviated as 100 h ethylene yield) are calculated using the following equations, respectively.

$$C_2H_4 \text{ selectivity in gas phase product} = \frac{2 \times |C_2H_4|}{\sum x \times |\text{products}|} \times 100\% \quad (1)$$

$$100h C_2H_4 \text{ yield} = 100 \times \frac{|C_2H_4|}{m_{cat}} \quad (2)$$

where $|C_2H_4|$ represents the number of moles of ethylene in the reaction products per hour; $|\text{products}|$ represents the number of moles of each reaction product per hour, $m_{cat}$ represents the mass of the catalyst, and x is the number of carbon atoms in the gas phase product. For example, for $CH_4$, x=1; for $C_2H_4$, x=2.

A catalyst evaluation device involved in the embodiments of the present disclosure includes a liquid chromatograph-mass spectrometer (LC-MS) and an online gas chromatography. During the reaction process, the composition of the gas-phase product in the reactor is monitored and analyzed in real time by the online gas chromatography, while a liquid phase product in the reactor is collected and analyzed by liquid chromatograph-mass spectrometer to obtain information on composition and characteristic parameters of the liquid phase product in the reaction.

The preparation route of the present disclosure is shown below:

where $R^1$-$R^5$ are independently selected from one of H atom, alkyl, alkoxy, phenol hydroxyl, alcohol hydroxyl, carbonyl, halogen, respectively.

Embodiment 1

Methanol and phenol are mixed according to a molar ratio of 8:1 at a feed rate of 1.0 mL/h. The raw material is gasified and passed into a reaction tube under nitrogen, with a flow rate of nitrogen is 30 mL/min. The catalyst A is NaX molecular sieve at an amount of 50 mg and a bed temperature of 320° C.; the catalyst B is KY molecular sieve at an amount of 150 mg and a bed temperature of 250-290° C. In order to enhance the mass and heat transfer, each of the catalyst A and the catalyst B is mixed with 400 mg of quartz sand with a mesh size of 20-40 mesh when loading. The gas phase product is detected and analyzed by the online gas chromatography, and the liquid phase product is collected and analyzed by the liquid chromatograph-mass spectrometer. The results obtained are shown in Table 1.

Embodiments 2-35

Referring to the method described in Embodiment 1, the experimental parameters adopted in Embodiments 2-35 are slightly different from Embodiment 1, and the specific experimental parameters and reaction properties are shown in Table 1.

TABLE 1

Summary of experimental parameters and reaction properties of the Embodiments

| Emb. No. | Type of phenol-like molecule | Molar ratio of methanol to phenol-like molecule | Catalyst A Type | Catalyst A Amount (mg) | Catalyst A Temperature (°C) | Catalyst B Type | Catalyst B Amount (mg) | Catalyst B Temperature (°C) | Ethylene Selectivity (%) | 100 h ethylene yield (mmol $C_2H_4$ $g^{-1}$ cat) |
|---|---|---|---|---|---|---|---|---|---|---|
| 1 | Phenol | 8 | NaX | 50 | 320 | KY | 150 | 290 | 97.3 | 221.1 |
| 2 | Phenol | 8 | NaX | 50 | 320 | KX | 150 | 360 | 96.3 | 113.6 |
| 3 | Phenol | 8 | NaX | 50 | 320 | K-beta | 150 | 360 | 96.5 | 107.5 |
| 4 | Phenol | 8 | NaX | 50 | 320 | HY | 150 | 360 | 59.6 | 141.2 |
| 5 | Phenol | 8 | NaX | 50 | 320 | SAPO-34 | 150 | 160 | 99.7 | 52.7 |
| 6 | Phenol | 8 | NaX | 50 | 320 | SAPO-34 | 150 | 200 | 99.3 | 155.8 |
| 7 | Phenol | 8 | NaX | 50 | 320 | SAPO-34 | 150 | 230 | 99.4 | 196.5 |
| 8 | Phenol | 8 | NaX | 50 | 320 | AlPO-18 | 150 | 400 | 99.1 | 189.7 |
| 9 | Phenol | 8 | NaX | 50 | 320 | SAPO-18 | 150 | 230 | 99.6 | 294.8 |
| 10 | Phenol | 8 | NaX | 50 | 320 | SAPO-11 | 150 | 230 | 99.3 | 79.8 |
| 11 | Phenol | 8 | NaX | 50 | 320 | SAPO-14 | 150 | 230 | 99.4 | 70.6 |
| 12 | Phenol | 8 | NaX | 50 | 320 | SSZ-13 | 150 | 350 | 99.8 | 503.6 |
| 13 | Phenol | 8 | NaX | 50 | 320 | ZSM-5 | 150 | 230 | 99.2 | 273.3 |
| 14 | Phenol | 8 | NaX | 50 | 320 | chaba | 150 | 300 | 99.3 | 168.9 |
| 15 | Phenol | 8 | NaY | 50 | 360 | SAPO-34 | 150 | 230 | 99.2 | 175.0 |
| 16 | Phenol | 8 | Na-beta | 50 | 400 | SAPO-34 | 150 | 230 | 98.7 | 61.4 |
| 17 | Phenol | 8 | γ-$Al_2O_3$ | 50 | 400 | SAPO-34 | 150 | 230 | 98.7 | 138.2 |
| 18 | Phenol | 8 | MgO | 50 | 400 | SAPO-34 | 150 | 230 | 98.7 | 9.2 |
| 19 | Phenol | 6 | NaX | 50 | 300 | SAPO-34 | 150 | 230 | 99.3 | 162.7 |
| 20 | Phenol | 4 | NaX | 50 | 340 | SAPO-34 | 150 | 230 | 99.7 | 168.9 |
| 21 | Phenol | 3 | NaX | 50 | 360 | SAPO-34 | 150 | 230 | 99.5 | 208.8 |
| 22 | Phenol | 2 | NaX | 50 | 380 | SAPO-34 | 150 | 230 | 98.9 | 129.0 |
| 23 | Phenol | 1 | NaX | 50 | 400 | SAPO-34 | 150 | 230 | 98.9 | 101.3 |
| 24 | Cresol | 3 | NaX | 50 | 360 | SAPO-34 | 150 | 230 | 99.6 | 531.2 |
| 25 | Ethyl-phenol | 3 | NaX | 50 | 360 | SAPO-34 | 150 | 230 | 99.9 | 525.1 |
| 26 | Propyl-phenol | 3 | NaX | 50 | 360 | SAPO-34 | 150 | 230 | 98.7 | 496.4 |
| 27 | 4-Methoxyphenol | 3 | NaX | 50 | 360 | SAPO-34 | 150 | 230 | 99.4 | 551.8 |
| 28 | 4-Ethoxyphenol | 3 | NaX | 50 | 360 | SAPO-34 | 150 | 230 | 99.4 | 531.3 |
| 29 | Hydroquinone | 3 | NaX | 50 | 360 | SAPO-34 | 150 | 230 | 98.7 | 215.8 |
| 30 | 4-(Hydroxymethyl)phenol | 3 | NaX | 50 | 360 | SAPO-34 | 150 | 230 | 99.4 | 426.8 |
| 31 | 4-Hydroxyacetophenone | 3 | NaX | 50 | 360 | SAPO-34 | 150 | 230 | 99.4 | 196.8 |
| 32 | 4-Hydroxybenzoic acid | 3 | NaX | 50 | 360 | SAPO-34 | 150 | 230 | 99.4 | 451.4 |
| 33 | Methyl 4-hydroxybenzoate | 3 | NaX | 50 | 360 | SAPO-34 | 150 | 230 | 99.4 | 186.2 |
| 34 | 4-Bromophenol | 3 | NaX | 50 | 360 | SAPO-34 | 150 | 230 | 99.4 | 104.2 |
| 35 | 4-Chlorophenol | 3 | NaX | 50 | 360 | SAPO-34 | 150 | 230 | 99.4 | 96.8 |

The process described in the present disclosure has a good stability and can be operated continuously for more than 100 h. A little coke is formed in catalyst during the reaction. In contrast, the conventional methanol-to-olefin (MTO) process is prone to coke deposition, the catalyst runs continuously for less than 10 h, and after a period of operation, the catalyst must be regenerated by air combustion to remove the coke before it can continue to be used. In the 100 h stability tests of Embodiments 1-38, the catalytic performance is maintained, and the 100 h ethylene yield, which is the amount of ethylene produced per gram of catalyst over the 100 h stable life cycle of the catalyst, is up to 551.8 mmol $C_2H_4$ $g^{-1}$ cat, which is higher than the amount of ethylene produced on conventional MTO catalysts (150-250 mmol $C_2H_4$ $g^{-1}$ cat) per gram of catalyst produced over a stable life cycle (10 h) (Ref: Álvaro-Muñoz, T., Márquez-Álvarez, C., Sastre, E. Applied Catalysis A: General. 472, 72-79 (2014). Tian, P., Wei, Y., Ye, M., Liu, Z. ACS Catalysis. 5(3), 1922-1938 (2015).).

Embodiments 1-14 illustrate the effect of the type of catalyst B on the reaction temperature, ethylene selectivity, and 100 h ethylene yield, when the catalyst A is fixed to NaX molecular sieve, the reaction temperature is fixed to 320° C., and the molecular catalyst is phenol. As can be seen from the table, the catalyst B may be one or a mixture of Y-type, X-type, AlPO, SAPO, SSZ, ZSM, chabazite, and more preferably SAPO-type molecular sieves. The best 100 h ethylene yield is achieved when the catalyst B is SAPO-34 and SAPO-18 molecular sieves. During the preparation process, when the catalyst B is selected from KY, KX, AlPO, SAPO, SSZ, ZSM, and chabazite molecular sieves, the ethylene selectivity can all be greater than 95%, while when the catalyst B is selected with the HY molecular sieve, the ethylene selectivity is only 60-70%.

Embodiments 7, 15-18 illustrate the effect of the type of the catalyst A on the reaction temperature, ethylene selectivity, and 100 h ethylene yield, when the catalyst B is fixed to SAPO-34 molecular sieve, the reaction temperature of the catalyst B is fixed to 230° C., and the molecular catalyst is fixed to phenol. As can be seen from the table, the catalyst A may be one or a mixture of X-type, Y-type, and β-type molecular sieves. The best 100 h ethylene yield is achieved when the catalyst A is NaX molecular sieve. During the preparation process, the 100 h ethylene yield is only 9.21 mmol $C_2H_4$ $g^{-1}$ cat when the catalyst A is MgO.

Embodiments 7, 19-23 illustrate the effect of the molar ratio of methanol to phenol-like molecules on the reaction temperature, the 100 h ethylene yield, and the ethylene selectivity, preferably 8:1-1:1, more preferably 3:1. During the testing process, optimization of the molar ratio of methanol to phenol-like molecules resulted in the modulation of the 100 h ethylene yields, with the highest 100 h ethylene yields up to 208.79 mmol $C_2H_4$ $g^{-1}$ cat.

Figure 1:
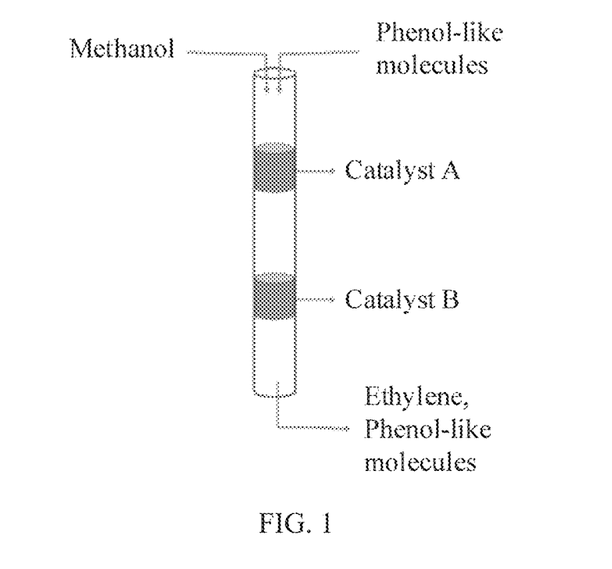
FIG. 1 is a schematic view of a two-stage fixed-bed catalytic reactor used in the present disclosure and a schematic diagram of a reaction process.
Figure 2:
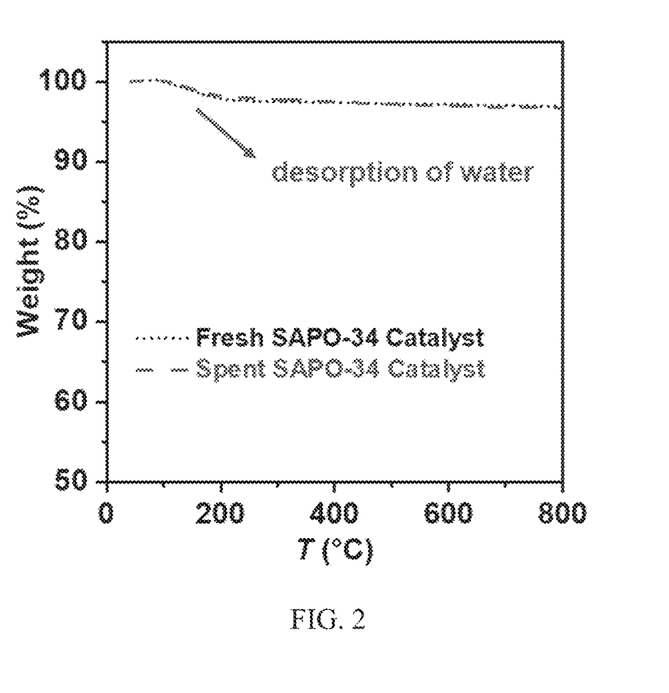
FIG. 2 shows a thermogravimetric diagram of SAPO-34 before and after the reaction in Embodiment 21.
Figure 3:
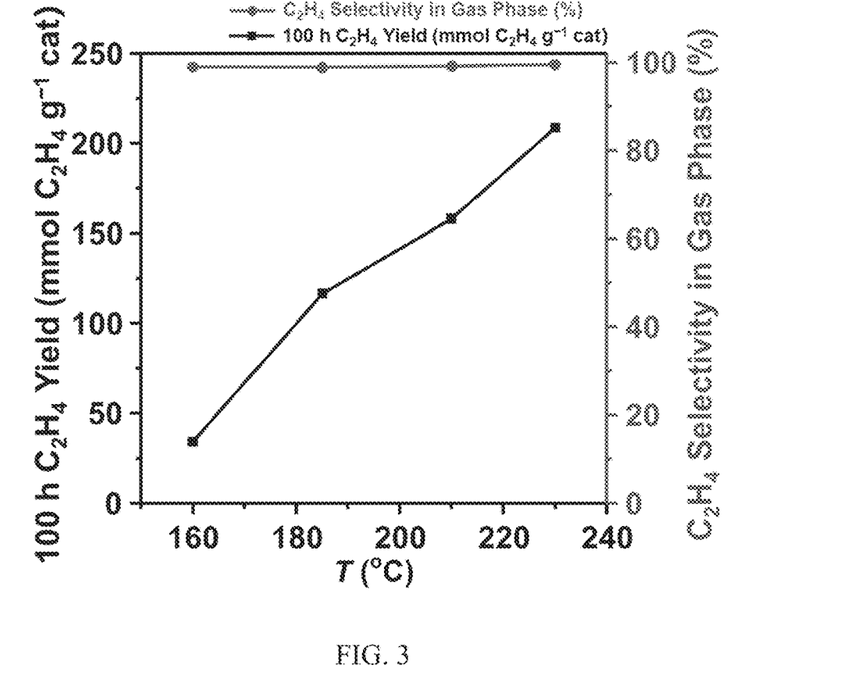
FIG. 3 shows a trend diagram of the reaction in Embodiment 21 as a function of temperature.
Figure 4:
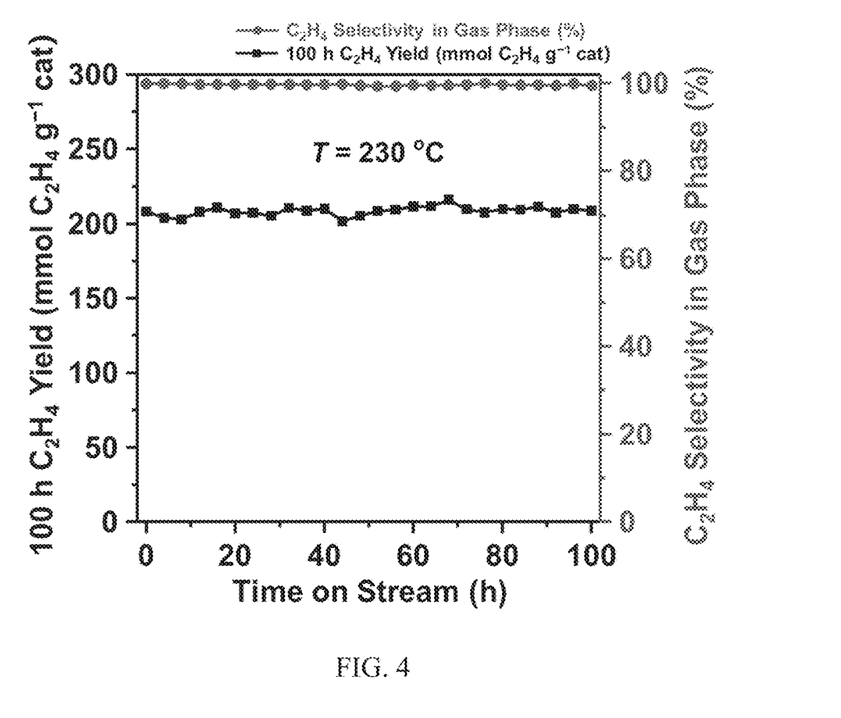
FIG. 4 shows a diagram of stability results of the catalytic reaction in Embodiment 21.

Taking Embodiment 21 as an example, the thermogravimetric curves of SAPO-34 before and after the reaction are shown in FIG. 2, and there is a little coke formed on the surface of the catalyst B after 100 h of reaction of SAPO-34, which proves the good catalytic stability of the reaction in the present disclosure; the trend of the reaction as a function of temperature is shown in FIG. 3, and the 100 h ethylene yield increases with the rise of the reaction temperature; when the reaction temperature is 230° C., the 100 h ethylene yield is achieved as 208.79 mmol $C_2H_4$ $g^{-1}$ cat and the ethylene selectivity is >99%; the catalytic stability performance is shown in FIG. 4, there is no significant decrease in the reaction performance within 100 h, which further indicates that the reaction process of the present disclosure has good catalytic stability.

Embodiments 21, 24-35 illustrate the effect of the type of phenol-like molecule on the ethylene selectivity and 100 h ethylene yield. The substituents may include one or more of H atoms, alkyl groups, alkoxy groups, phenol hydroxyl groups, alcohol hydroxyl groups, carbonyl groups, and halogens. The ethylene selectivity is each greater than 98%, and the 100 h ethylene yield is up to 551.79 mmol $C_2H_4$ $g^{-1}$ cat when the phenol-like molecule is a methoxy phenol.

Embodiment 36

Referring to the method described in Embodiment 21, methanol is mixed with phenol at a molar ratio of 3:1 at a feed rate of 1.0 mL/h. The raw material is gasified and passed into the reaction tube under nitrogen, varying the flow rate of nitrogen to 100, 80, 60, 40, 30, 20, 0 mL/min. The catalyst A is NaX molecular sieve at an amount of 50 mg and a bed temperature of 360° C. The catalyst B is SAPO-34 molecular sieve at an amount of 150 mg and a bed temperature of 230° C. To enhance the mass and heat transfer, each of the catalyst A and the catalyst B is mixed with 400 mg of quartz sand with a mesh size of 20-40 mesh when loading. The gas phase product is detected and analyzed by the online gas chromatography, and the liquid phase product is collected and analyzed by the liquid chromatograph-mass spectrometer. With the gradual decrease of nitrogen flow rate from 100 to 0 mL/min, the ethylene selectivity in the gas phase product is greater than 99%. The 100 h ethylene yield shows an increasing and then decreasing trend with the decrease of nitrogen flow rate. When the nitrogen flow rate is 30 mL/min, the 100 h ethylene yield reaches the highest value of 208.8 mmol $C_2H_4$ $g^{-1}$ cat. When the nitrogen flow rate is 100 mL/min, the 100 h ethylene yield is 83.31 mmol $C_2H_4$ $g^{-1}$ cat. When the nitrogen flow rate is 0 mL/min, the 100 h ethylene yield is 98.06 mmol $C_2H_4$ $g^{-1}$ cat.

Embodiment 37

Referring to the method described in Embodiment 21, methanol is mixed with phenol at a molar ratio of 3:1, varying the feed rate with the methanol space velocity of 3, 6, 9, 40, 80, 120, 160, 200 kg $CH_3OH$/(kg cat. A)/h, and the nitrogen flow rate is 30 mL/min. The raw material is gasified and passed into the reaction tube under nitrogen. The catalyst A is NaX molecular sieve at an amount of 50 mg at a bed temperature of 360° C., and the catalyst B is SAPO-34 molecular sieve at an amount of 150 mg at a bed temperature of 230° C. To enhance the mass and heat transfer, each of the catalyst A and the catalyst B is mixed with 400 mg of quartz sand with a mesh size of 20-40 mesh when loading. The gas phase product is detected and analyzed by the online gas chromatography, and the liquid phase product is collected and analyzed by the liquid chromatograph-mass spectrometer. It is found that the ethylene selectivity in the gas phase product is greater than 99% with the gradual increase of methanol space velocity from 3 to 200 kg $CH_3OH$/(kg cat. A)/h. The 100 h ethylene yield shows an increasing and then decreasing trend with the increase of methanol space velocity. When the methanol space velocity is 24 kg $CH_3OH$/(kg cat. A)/h, the 100 h ethylene yield reaches the highest value of 201.2 mmol $C_2H_4$ $g^{-1}$ cat. When the methanol space velocity is 3 kg $CH_3OH$/(kg cat. A)/h, the 100 h ethylene yield is 181.3 mmol $C_2H_4$ $g^{-1}$ cat. When the methanol space velocity is 200 kg $CH_3OH$/(kg cat. A)/h, the 100 h ethylene yield is 109.8 mmol $C_2H_4$ $g^{-1}$ cat.

Embodiment 38

Referring to the method described in Embodiment 21, methanol is mixed with phenol at a molar ratio of 3:1 at a feed rate of 1.0 mL/h and a nitrogen flow rate of 30 mL/min. The raw material is gasified and passed into the reaction tube under nitrogen. The catalyst A is NaX molecular sieve at a bed temperature of 360° C., and the catalyst B is SAPO-34 molecular sieve at a bed temperature of 230° C., varying the catalyst A/B mass ratio of 0.1, 0.33, 1, 3, 6, 9, 12. To enhance the mass and heat transfer, each of the catalyst A and the catalyst B is mixed with 400 mg of quartz sand with a mesh size of 20-40 mesh when loading. The gas phase product is detected and analyzed by the online gas chromatography, and the liquid phase product is collected and analyzed by the liquid chromatograph-mass spectrometer. It is found that the ethylene selectivity in the gas phase product is greater than 99% with the gradual increase of the catalyst A/B mass ratio from 0.1 to 12, and the 100 h ethylene yield shows an increasing and then decreasing trend with the increase of the catalyst A/B mass ratio. When the catalyst A/B mass ratio is 0.1, the 100 h ethylene yield reaches the highest value of 208.8 mmol $C_2H_4$ $g^{-1}$ cat. When the catalyst A/B mass ratio is 0.33, the 100 h ethylene yield is 133.1 mmol $C_2H_4$ $g^{-1}$ cat. When the catalyst A/B mass ratio is 12, the 100 h ethylene yield is 118.3 mmol $C_2H_4$ $g^{-1}$ cat.

Comparative Example 1

This comparative example is carried out with reference to the reaction parameters of Embodiment 21, and differs from Embodiment 21 in that no catalyst B is added. The gas and liquid phase products are detected by chromatography, showing that the main product is anisole and that ethylene is not present. This result indicates that the primary role of the catalyst A is to catalyze the reaction between methanol and phenol to produce anisole molecules. Highly selective ethylene-production from methanol cannot be achieved with only the catalyst A and the molecular catalyst, namely, the phenol-like molecules.

Comparative Example 2

Anisole is used as the raw material, the feed rate is 1 mL/h, and the raw material is gasified and passed into the reaction tube driven by nitrogen, with a nitrogen flow rate of 30 mL/min. The catalyst is SAPO-34 molecular sieve at an amount of 150 mg. To enhance the mass transfer and heat transfer, the catalyst is loaded with 400 mg of quartz sand mixed with a mesh size of 20-40 mesh when loading. During the test, the bed temperature is in a range of 160-230° C. The gas phase product is detected and analyzed by the online gas chromatography, and the liquid phase product is collected and analyzed by the liquid chromatograph-mass spectrometer. It is found that the main product of anisole decomposition is ethylene and phenol, the ethylene selectivity in the gas-phase product is >98%, and the phenol selectivity in the liquid phase product is >91%; the 100 h ethylene yield increases with the increase of temperature. The 100 h ethylene yield is 62.7 mmol $C_2H_4$ $g^{-1}$ cat at 160° C., and 218.8 mmol $C_2H_4$ $g^{-1}$ cat at 230° C. This result suggests that the main role of the catalyst B is to catalyze the decomposition of anisole into phenol and ethylene.

Comparative Example 3

This comparative example is carried out according to the reaction parameters of Embodiment 21, and differs from Embodiment 21 in that no catalyst A is added. The gas and liquid phase products are detected by chromatography, showing that no ethylene is produced, even at a reaction temperature of 230° C.

Comparative Example 4

This comparative example is carried out according to the reaction parameters of Embodiment 21, and differs from Embodiment 21 in that no phenol is added n. The gas and liquid phase products are detected by chromatography, showing that even if the reaction temperature of the catalyst B is 230° C., the methanol as raw material is hardly reacted, and no ethylene is produced in the gas phase.

Figure 5:
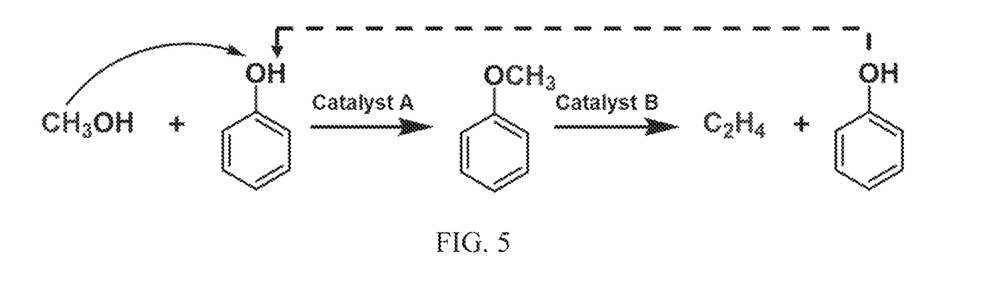
FIG. 5 shows a reaction principle of a process for a highly selective preparation of ethylene from methanol according to the present disclosure.

As can be seen from the synthesis of Embodiment 21 and Comparative Examples 1-4, the molecular catalyst, the catalyst A, and the catalyst B are indispensable in the methanol-to-ethylene process proposed in the present disclosure. The synergistic effect between them is the key to ensure the high selective conversion of methanol to ethylene. The specific reaction process is shown in FIG. 5, where methanol reacts with the phenol-like molecules to generate anisole-like molecules under the action of the catalyst A. Subsequently, the anisole-like molecules decompose to generate the phenol-like molecules and ethylene under the action of the catalyst B, where the phenol-like molecules participate in the reaction, but the quantity thereof before and after the reaction does not change significantly, and thus the phenol-like molecules act as the molecular catalyst. And as can be seen from Embodiments 1-38, factors such as the types of catalysts A and B, the reaction temperature, and the ratio of phenol-like molecules to methanol affect the catalytic reaction performance.

What is claimed is:

1. A method of preparing olefins from methanol, comprising:
taking the methanol and phenol molecules as raw materials;
gasifying the raw materials and passing into a two-stage fixed-bed catalytic reactor under an anaerobic environment, such that ethylene is generated after a reaction, wherein the reaction lasts for 100 hours;
wherein the two-stage fixed-bed catalytic reactor comprises a first constant-temperature zone and a second constant-temperature zone in an order from an inlet to an outlet,
wherein the first constant-temperature zone is at a temperature of 300° C. to 400° C.,
wherein the second constant-temperature zone is at a temperature of 160° C. to 400° C.;
placing a catalyst A in the first constant-temperature zone; and
placing a catalyst B is placed in the second constant-temperature zone;
wherein the catalyst A is a silica-aluminum molecular sieve;
wherein the catalyst B is a silica-aluminum molecular sieve or a phosphorus-aluminum molecular sieve; and
wherein the phenol molecules represented by a structural formula as listed below:

wherein $R^1$-$R^5$ are independently selected from one of H atom, alkyl, alkoxy, phenol hydroxyl, alcohol hydroxyl, halogen, respectively; and R' is selected from one of H atom, hydroxyl, alkoxy, alkyl, and amino.

2. The method according to claim 1, wherein a molar ratio of the methanol to the phenol molecules is 1:1 to 8:1.

3. The method according to claim 1, wherein the first constant-temperature zone is at a temperature of 320° C. to –360° C.

4. The method according to claim 1, wherein the second constant-temperature zone is at a temperature of 200° C. to –300° C.

5. The method according to claim 1, wherein further comprising: introducing an inert gas, wherein the inert gas is mixed with the gasified raw materials.

6. The method according to claim 5, wherein the inert gas is one or more of $N_2$, He, or Ar.

7. The method according to claim 5, wherein a flow rate of the inert gas is 0 mL/min to 100 mL/min.

8. The method according to claim 1, wherein quartz sand is added to the first constant-temperature zone of the two-stage fixed-bed catalytic reactor, and wherein the quartz sand is mixed with the catalyst A.

9. The method according to claim 1, wherein quartz sand is added to the second constant-temperature zone of the two-stage fixed-bed catalytic reactor, and wherein the quartz sand is mixed with the catalyst B.

10. The method according to claim 1, wherein a space velocity of the methanol is 3 kg $CH_3OH$/(kg cat. A)/h to 200 kg $CH_3OH$/(kg cat. A)/h.

11. The method according to claim 1, wherein a mass ratio of the catalyst A/catalyst B is 0.1 to 12.

* * * * *